(12) United States Patent
Netzel et al.

(10) Patent No.: US 12,048,472 B2
(45) Date of Patent: Jul. 30, 2024

(54) ELECTROSURGICAL INSTRUMENTS, JAW MEMBERS THEREOF, AND METHODS OF MANUFACTURING

(71) Applicant: Covidien LP, Mansfield, MA (US)

(72) Inventors: Kenneth E. Netzel, Loveland, CO (US); James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 548 days.

(21) Appl. No.: 17/163,693

(22) Filed: Feb. 1, 2021

(65) Prior Publication Data

US 2022/0241005 A1    Aug. 4, 2022

(51) Int. Cl.
*A61B 18/14*      (2006.01)
*A61B 17/00*      (2006.01)
*A61B 18/00*      (2006.01)

(52) U.S. Cl.
CPC ...... *A61B 18/1442* (2013.01); *A61B 2017/00526* (2013.01); *A61B 2018/00083* (2013.01); *A61B 2018/00589* (2013.01); *A61B 2018/00595* (2013.01); *A61B 2018/0063* (2013.01); *A61B 18/1445* (2013.01)

(58) Field of Classification Search
CPC .......... A61B 17/282; A61B 2017/2825; A61B 2017/2926; A61B 18/1445; A61B 18/1442
See application file for complete search history.

(56) References Cited

U.S. PATENT DOCUMENTS

| | | |
|---|---|---|
| 2,068,721 A | 1/1937 | Wappler |
| 4,091,813 A | 5/1978 | Shaw et al. |
| 4,984,564 A | 1/1991 | Yuen |
| 5,007,926 A | 4/1991 | Derbyshire |
| 5,037,379 A | 8/1991 | Clayman et al. |

(Continued)

FOREIGN PATENT DOCUMENTS

| | | |
|---|---|---|
| EP | 2353535 A1 | 8/2011 |
| EP | 2510890 A2 | 10/2012 |

(Continued)

OTHER PUBLICATIONS

Extended European Search Report issued in corresponding European Application No. 22154396.0 dated Jun. 30, 2022, 10 pages.

*Primary Examiner* — Linda C Dvorak
*Assistant Examiner* — Ryan T Clark
(74) *Attorney, Agent, or Firm* — Carter, DeLuca & Farrell LLP

(57) ABSTRACT

A jaw member of an electrosurgical instrument includes an insulative spacer including a face and defining first and second elongated recesses on either side of the face, first and second cleats disposed at least partially within the first and second elongated recesses, respectively, a structural frame, and a tissue treating plate. The structural frame is configured to receive at least a portion of the insulative spacer therein such that first and second elongated sides of the structural frame at least partially overlap the first and second cleats, respectively. The first and second elongated sides are engaged with the first and second cleats, respectively, to thereby secure the insulative spacer relative to the structural frame with the face exposed. The tissue treating plate is disposed on the face of the insulative spacer and is adapted to connect to a source of energy to treat tissue therewith.

19 Claims, 9 Drawing Sheets

(56) References Cited

U.S. PATENT DOCUMENTS

| | | | |
|---|---|---|---|
| 5,078,726 A | 1/1992 | Kreamer |
| 5,143,082 A | 9/1992 | Kindberg et al. |
| 5,159,921 A | 11/1992 | Hoover |
| 5,171,262 A | 12/1992 | MacGregor |
| 5,176,659 A | 1/1993 | Mancini |
| 5,213,114 A | 5/1993 | Bailey, Jr. |
| 5,215,101 A | 6/1993 | Jacobs et al. |
| 5,215,521 A | 6/1993 | Cochran et al. |
| 5,224,930 A | 7/1993 | Spaeth et al. |
| 5,231,974 A | 8/1993 | Giglio et al. |
| 5,308,327 A | 5/1994 | Heaven et al. |
| 5,312,416 A | 5/1994 | Spaeth et al. |
| 5,330,483 A | 7/1994 | Heaven et al. |
| 5,354,303 A | 10/1994 | Spaeth et al. |
| 5,374,272 A | 12/1994 | Arpa et al. |
| 5,380,304 A | 1/1995 | Parker |
| 5,389,098 A | 2/1995 | Tsuruta et al. |
| 5,403,312 A | 4/1995 | Yates et al. |
| 5,411,549 A | 5/1995 | Peters |
| 5,441,515 A | 8/1995 | Khosravi et al. |
| 5,449,382 A | 9/1995 | Dayton |
| 5,465,895 A | 11/1995 | Knodel et al. |
| 5,520,610 A | 5/1996 | Giglio et al. |
| 5,578,075 A | 11/1996 | Dayton |
| 5,611,803 A | 3/1997 | Heaven et al. |
| 5,618,296 A | 4/1997 | Sorensen et al. |
| 5,636,639 A | 6/1997 | Turturro et al. |
| 5,649,550 A | 7/1997 | Crook |
| 5,707,385 A | 1/1998 | Williams |
| 5,769,794 A | 6/1998 | Conlan et al. |
| 5,785,677 A | 7/1998 | Auweiler |
| 5,810,721 A | 9/1998 | Mueller et al. |
| 5,810,811 A | 9/1998 | Yates et al. |
| 5,814,044 A | 9/1998 | Hooven |
| 5,827,271 A | 10/1998 | Buysse et al. |
| 5,833,690 A | 11/1998 | Yates et al. |
| 5,876,401 A | 3/1999 | Schulze et al. |
| 5,906,577 A | 5/1999 | Beane et al. |
| 5,911,719 A | 6/1999 | Eggers |
| 5,957,888 A | 9/1999 | Hinchliffe |
| 5,971,995 A | 10/1999 | Rousseau |
| 5,993,427 A | 11/1999 | Rolland et al. |
| 6,024,741 A | 2/2000 | Williamson, IV et al. |
| 6,027,779 A | 2/2000 | Campbell et al. |
| 6,039,748 A | 3/2000 | Savage et al. |
| 6,048,309 A | 4/2000 | Flom et al. |
| 6,059,793 A | 5/2000 | Pagedas |
| 6,086,586 A | 7/2000 | Hooven |
| 6,090,136 A | 7/2000 | McDonald et al. |
| 6,162,172 A | 12/2000 | Cosgrove et al. |
| 6,206,889 B1 | 3/2001 | Bennardo |
| 6,228,095 B1 | 5/2001 | Dennis |
| 6,258,102 B1 | 7/2001 | Pagedas |
| 6,273,887 B1 | 8/2001 | Yamauchi et al. |
| 6,350,267 B1 | 2/2002 | Stefanchik |
| 6,382,211 B1 | 5/2002 | Crook |
| 6,387,102 B2 | 5/2002 | Pagedas |
| 6,402,747 B1 | 6/2002 | Lindemann et al. |
| 6,406,440 B1 | 6/2002 | Stefanchik |
| 6,602,252 B2 | 8/2003 | Mollenauer |
| 6,736,813 B2 | 5/2004 | Yamauchi et al. |
| 6,776,780 B2 | 8/2004 | Mulier et al. |
| 6,802,843 B2 | 10/2004 | Truckai et al. |
| 6,808,525 B2 | 10/2004 | Latterell et al. |
| 6,814,700 B1 | 11/2004 | Mueller et al. |
| 6,821,273 B2 | 11/2004 | Mollenauer |
| 6,860,880 B2 | 3/2005 | Treat et al. |
| 6,899,710 B2 | 5/2005 | Hooven |
| 6,929,641 B2 | 8/2005 | Goble et al. |
| 6,953,461 B2 | 10/2005 | McClurken et al. |
| 7,011,656 B2 | 3/2006 | McGaffigan et al. |
| 7,033,356 B2 | 4/2006 | Latterell et al. |
| 7,070,597 B2 | 7/2006 | Truckai et al. |
| 7,083,619 B2 | 8/2006 | Truckai et al. |
| 7,112,201 B2 | 9/2006 | Truckai et al. |
| 7,125,409 B2 | 10/2006 | Truckai et al. |
| 7,147,637 B2 | 12/2006 | Goble |
| 7,169,146 B2 | 1/2007 | Truckai et al. |
| 7,204,835 B2 | 4/2007 | Latterell et al. |
| 7,270,664 B2 | 9/2007 | Johnson et al. |
| 7,276,068 B2 | 10/2007 | Johnson et al. |
| 7,326,202 B2 | 2/2008 | McGaffigan |
| 7,329,255 B2 | 2/2008 | McGaffigan |
| 7,354,440 B2 | 4/2008 | Truckal et al. |
| 7,357,802 B2 | 4/2008 | Palanker et al. |
| 7,364,577 B2 | 4/2008 | Wham et al. |
| 7,396,356 B2 | 7/2008 | Mollenauer |
| 7,419,490 B2 | 9/2008 | Falkenstein et al. |
| 7,547,310 B2 | 6/2009 | Whitfield |
| 7,670,346 B2 | 3/2010 | Whitfield |
| 7,686,827 B2 | 3/2010 | Hushka |
| 7,691,120 B2 | 4/2010 | Shluzas et al. |
| 7,815,641 B2 | 10/2010 | Dodde et al. |
| 7,931,649 B2 | 4/2011 | Couture et al. |
| 8,034,051 B2 | 10/2011 | Martin et al. |
| 8,075,567 B2 | 12/2011 | Taylor et al. |
| 8,162,940 B2 | 4/2012 | Johnson et al. |
| 8,187,273 B2 | 5/2012 | Kerr et al. |
| 8,197,472 B2 | 6/2012 | Lau et al. |
| 8,206,294 B2 | 6/2012 | Widenhouse et al. |
| 8,226,649 B2 | 7/2012 | Falkenstein et al. |
| 8,292,879 B2 | 10/2012 | Manwaring et al. |
| 8,303,585 B2 | 11/2012 | Mollenauer |
| 8,372,066 B2 | 2/2013 | Manwaring et al. |
| 8,377,052 B2 | 2/2013 | Manwaring et al. |
| 8,394,094 B2 | 3/2013 | Edwards et al. |
| 8,409,112 B2 | 4/2013 | Wynne et al. |
| 8,409,216 B2 | 4/2013 | Parihar et al. |
| 8,414,596 B2 | 4/2013 | Parihar et al. |
| 8,425,503 B2 | 4/2013 | Manwaring et al. |
| 8,425,533 B2 | 4/2013 | Parihar et al. |
| 8,491,578 B2 | 7/2013 | Manwaring et al. |
| 8,491,626 B2 | 7/2013 | Roy et al. |
| 8,523,850 B2 | 9/2013 | Manwaring et al. |
| 8,523,852 B2 | 9/2013 | Manwaring et al. |
| 8,540,628 B2 | 9/2013 | O'Prey et al. |
| 8,551,088 B2 | 10/2013 | Falkenstein et al. |
| 8,562,598 B2 | 10/2013 | Falkenstein et al. |
| 8,568,411 B2 | 10/2013 | Falkenstein et al. |
| 8,579,914 B2 | 11/2013 | Menn et al. |
| 8,597,180 B2 | 12/2013 | Copeland et al. |
| 8,597,293 B2 | 12/2013 | Falkenstein et al. |
| 8,597,297 B2 | 12/2013 | Couture et al. |
| 8,617,151 B2 | 12/2013 | Denis et al. |
| 8,623,003 B2 | 1/2014 | Lau et al. |
| 8,636,730 B2 | 1/2014 | Keppel |
| 8,734,445 B2 | 5/2014 | Johnson et al. |
| 8,740,904 B2 | 6/2014 | Stopek |
| 8,777,849 B2 | 7/2014 | Haig et al. |
| 8,864,658 B2 | 10/2014 | Wilkins et al. |
| 8,915,909 B2 | 12/2014 | Manwaring et al. |
| 8,932,279 B2 | 1/2015 | Stringham et al. |
| 8,951,248 B2 | 2/2015 | Messerly et al. |
| 8,961,408 B2 | 2/2015 | Wilkins et al. |
| 8,968,329 B2 | 3/2015 | Cabrera |
| 8,986,321 B2 | 3/2015 | Parihar et al. |
| 9,005,199 B2 | 4/2015 | Beckman et al. |
| 9,017,340 B2 | 4/2015 | Davis |
| 9,039,694 B2 | 5/2015 | Ross et al. |
| 9,050,100 B2 | 6/2015 | Yates et al. |
| 9,084,606 B2 | 7/2015 | Greep |
| 9,119,630 B2 * | 9/2015 | Townsend .............. A61B 18/00 |
| 9,131,977 B2 | 9/2015 | Manwaring et al. |
| 9,149,321 B2 | 10/2015 | Stringham et al. |
| 9,192,427 B2 | 11/2015 | Johnson et al. |
| 9,265,553 B2 | 2/2016 | Manwaring et al. |
| 9,265,554 B2 | 2/2016 | Manwaring et al. |
| 9,265,555 B2 | 2/2016 | Manwaring et al. |
| 9,265,556 B2 | 2/2016 | Manwaring et al. |
| 9,320,560 B2 | 4/2016 | Manwaring et al. |
| 9,375,245 B2 * | 6/2016 | Roy .................. A61B 18/085 |
| 9,387,037 B2 | 7/2016 | Yang |
| 9,402,679 B2 | 8/2016 | Ginnebaugh et al. |
| 9,579,146 B2 | 2/2017 | Johnson et al. |

(56) References Cited

U.S. PATENT DOCUMENTS

| | | |
|---|---|---|
| 9,877,893 B2 | 1/2018 | Taylor et al. |
| 9,918,774 B2 | 3/2018 | Batchelor et al. |
| 9,931,157 B2 | 4/2018 | Strobl et al. |
| 9,955,858 B2 | 5/2018 | Pamnani et al. |
| 10,085,794 B2 | 10/2018 | Kerr et al. |
| 10,204,773 B2 | 2/2019 | Sugiyama et al. |
| 10,213,247 B2 | 2/2019 | Manwaring et al. |
| 10,639,091 B2 * | 5/2020 | Jones ................. A61B 18/1442 |
| 2004/0078035 A1 | 4/2004 | Kanehira et al. |
| 2005/0267492 A1 | 12/2005 | Poncet et al. |
| 2006/0200169 A1 | 9/2006 | Sniffin |
| 2006/0200170 A1 | 9/2006 | Aranyi |
| 2007/0265616 A1 | 11/2007 | Couture et al. |
| 2010/0312189 A1 | 12/2010 | Shelton, IV et al. |
| 2011/0184311 A1 | 7/2011 | Parihar et al. |
| 2011/0190779 A1 | 8/2011 | Gell et al. |
| 2011/0282237 A1 | 11/2011 | Conlon |
| 2011/0319719 A1 | 12/2011 | O'Prey et al. |
| 2012/0083795 A1 | 4/2012 | Fleming et al. |
| 2012/0157777 A1 | 6/2012 | Okoniewski |
| 2013/0014375 A1 | 1/2013 | Hempstead et al. |
| 2013/0046303 A1 | 2/2013 | Evans et al. |
| 2013/0232753 A1 | 9/2013 | Ackley et al. |
| 2013/0325025 A1 | 12/2013 | Hathaway et al. |
| 2014/0052018 A1 | 2/2014 | Hawkins |
| 2014/0135804 A1 | 5/2014 | Weisenburgh, II et al. |
| 2014/0194875 A1 | 7/2014 | Reschke et al. |
| 2015/0051598 A1 | 2/2015 | Orszulak et al. |
| 2016/0074099 A1 * | 3/2016 | Kappus .............. A61B 18/1445 29/434 |
| 2017/0156788 A1 | 6/2017 | Johnson et al. |
| 2017/0196648 A1 | 7/2017 | Ward et al. |
| 2018/0303322 A1 | 10/2018 | Pamnani et al. |
| 2019/0000538 A1 | 1/2019 | Widenhouse et al. |
| 2021/0022798 A1 | 1/2021 | Hammerland, III |

FOREIGN PATENT DOCUMENTS

| | | |
|---|---|---|
| WO | 2013015988 A1 | 1/2013 |
| WO | 2014120442 A2 | 8/2014 |
| WO | 2014158458 A1 | 10/2014 |
| WO | 2015017989 A1 | 2/2015 |

* cited by examiner

ELECTROSURGICAL INSTRUMENTS, JAW MEMBERS THEREOF, AND METHODS OF MANUFACTURING

FIELD

The present disclosure relates to surgical instruments and, more particularly, to electrosurgical instruments, jaw members thereof, and methods of manufacturing the same.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is farther from an operator (whether a human surgeon or a surgical robot), while the term "proximal" refers to the portion that is being described which is closer to the operator. Further, to the extent consistent, any or all of the aspects detailed herein may be used in conjunction with any or all of the other aspects detailed herein.

Provided in accordance with aspects of the present disclosure is a jaw member of an electrosurgical instrument. The jaw member includes an insulative spacer, first and second cleats, a structural frame, and a tissue treating plate. The insulative spacer includes a face and defines first and second elongated recesses on either side of the face. The first and second cleats are disposed at least partially within the first and second elongated recesses, respectively. The structural frame is configured to receive at least a portion of the insulative spacer therein such that first and second elongated sides of the structural frame at least partially overlap the first and second cleats, respectively. The first and second elongated sides are engaged with the first and second cleats, respectively, to thereby secure the insulative spacer relative to the structural frame with the face exposed. The tissue treating plate is disposed on the face of the insulative spacer and adapted to connect to a source of energy to treat tissue therewith.

In an aspect of the present disclosure, the first and second elongated sides are engaged with the first and second cleats, respectively, through cut outs defined within the first and second elongated sides. In such aspects, the first and second elongated sides may be welded or otherwise engaged to the first and second cleats, respectively, through the cut outs.

In another aspect of the present disclosure, the insulative spacer includes a body and first and second overhangs extending from the body. The body and the overhangs cooperate to define the face. In such aspects, the first and second elongated recesses may be undercut below the first and second overhangs, respectively.

In still another aspect of the present disclosure, the structural frame includes a distal body portion configured to receive the at least a portion of the insulative spacer. The distal body portion define an arcuate configuration including an inner concave face, an outer convex face, and the first and second elongated sides.

In yet another aspect of the present disclosure, the structural frame defines an aperture at least partially therethrough and the insulative spacer includes an alignment boss protruding therefrom. The alignment boss is received at least partially within the aperture to align the insulative spacer relative to the structural frame.

In still yet another aspect of the present disclosure, the insulative spacer includes a distal cap that overhangs a distal end of the structural frame to define a distal tip of the jaw member.

In another aspect of the present disclosure, an outer insulative jacket is disposed about at least a portion of an outer face of the structural frame.

In another aspect of the present disclosure, the tissue treating plate defines a longitudinally extending slot therethrough that exposes a portion of the face of the insulative spacer.

An electrosurgical instrument provided in accordance with aspects of the present disclosure includes first and second jaw members pivotably coupled to one another such that at least one of the first or second jaw members is movable relative to the other from a spaced-apart position to an approximated position to grasp tissue therebetween. One or both of the first or second jaw members may be configured similar to any of the aspects detailed above or otherwise herein. The tissue treating plates of the jaw members are configured to oppose one another in the approximated position of the first and second jaw members and are adapted to connect to a source of energy to treat tissue grasped therebetween.

In aspects of the present disclosure, one of the first or second jaw members includes a thermal cutting element supported partially within the insulative spacer and extending towards the other jaw member.

A method of manufacturing a jaw member of an electrosurgical instrument in accordance with the present disclosure includes inserting first and second cleats into first and second elongated recess, respectively, defined within an insulative spacer, inserting the insulative spacer, including the first and second cleats disposed therein, at least partially into a structural frame such that first and second elongated sides of the structural frame at least partially overlap the first and second cleats, and engaging the first and second elongated sides with the first and second cleats, respectively, to thereby secure the insulative spacer relative to the structural frame. The engaging may include welding. The method may further include providing a tissue treating plate on an exposed face of the insulative spacer.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
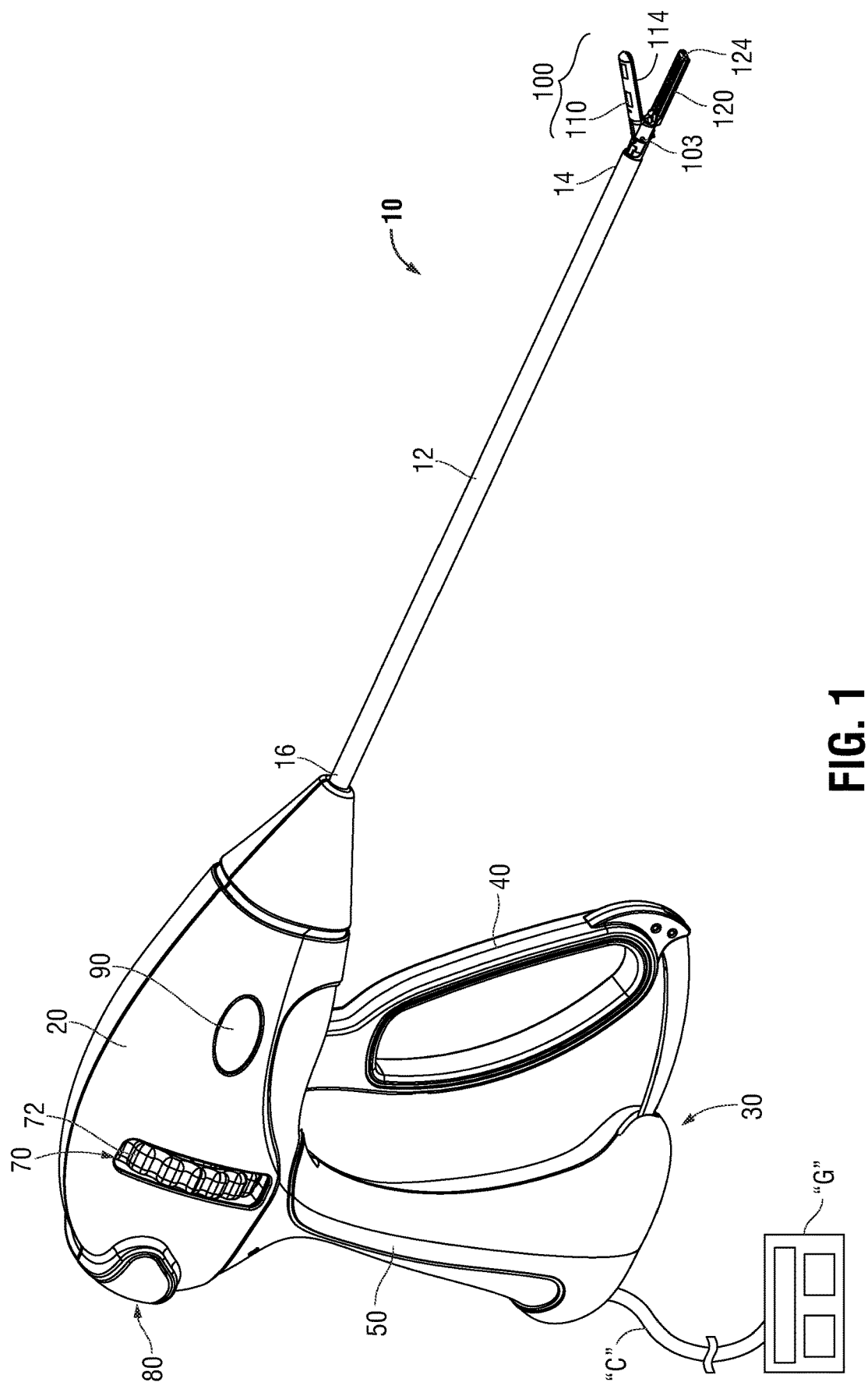
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue treating surfaces 114, 124 of jaw members 110, 120, respectively, of end effector assembly 100 to provide energy thereto. First activation switch 80 is coupled to tissue treating surfaces 114, 124 and the electrosurgical generator "G" for enabling the selective activation of the supply of energy to jaw members 110, 120 for treating, e.g., cauterizing, coagulating/desiccating, and/or sealing, tissue. Second activation switch 90 is coupled to thermal cutting element 130 of jaw member 120 (FIG. 4) and the electrosurgical generator "G" for enabling the selective activation of the supply of energy to thermal cutting element 130 for thermally cutting tissue.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced apart position and an approximated position to grasp tissue between tissue treating surfaces 114, 124 of jaw members 110, 120. As shown in FIG. 1, movable handle 40 is initially spaced apart from fixed handle 50 and, correspondingly, jaw members 110, 120 of end effector assembly 100 are disposed in the spaced apart position. Movable handle 40 is depressible from this initial position towards fixed handle 50 to a depressed position corresponding to the approximated position of jaw members 110, 120. Rotating assembly 70 includes a rotation wheel 72 that is selectively rotatable in either direction to correspondingly rotate shaft 12 and end effector assembly 100 relative to housing 20.

Figure 2:
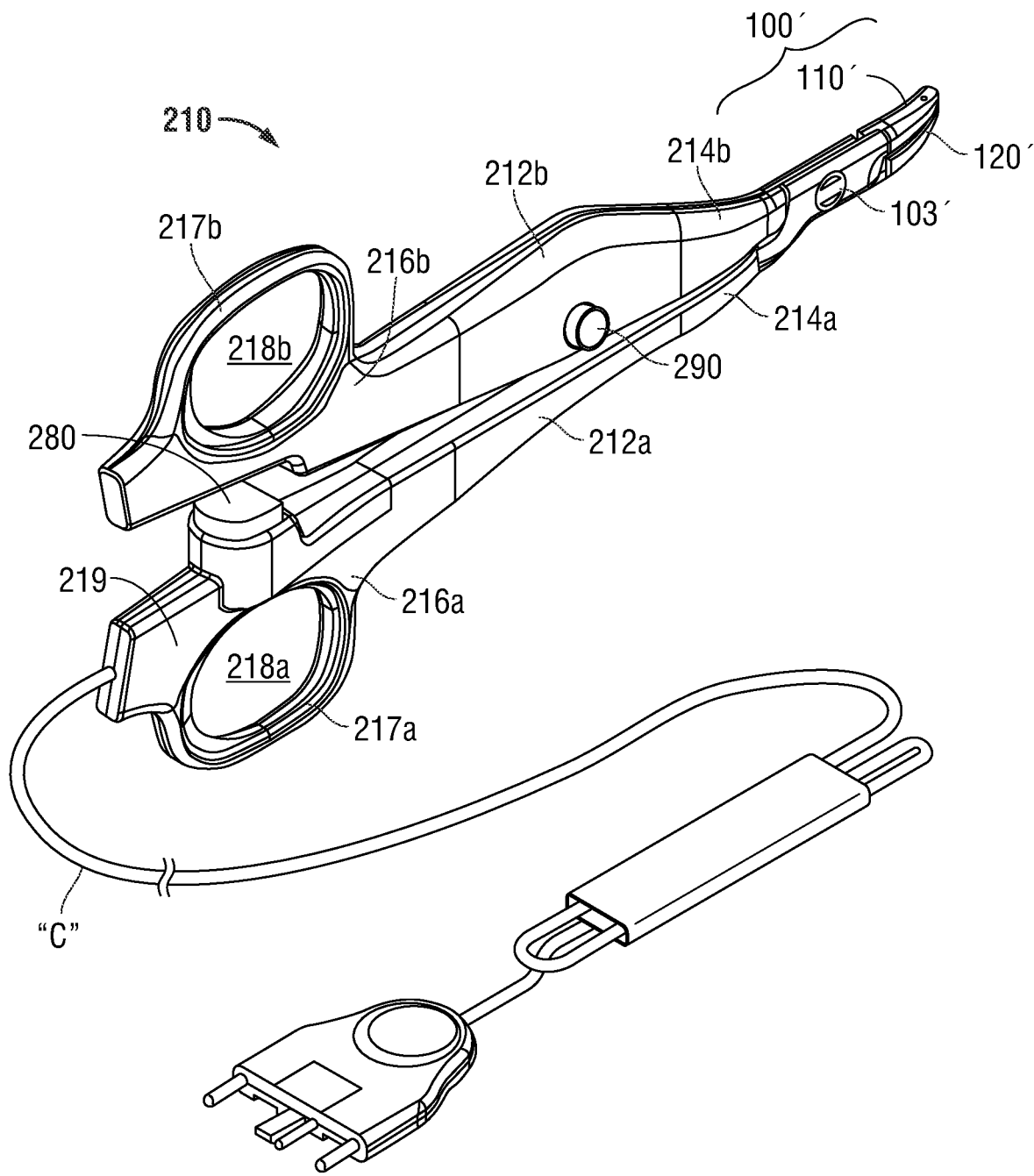
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
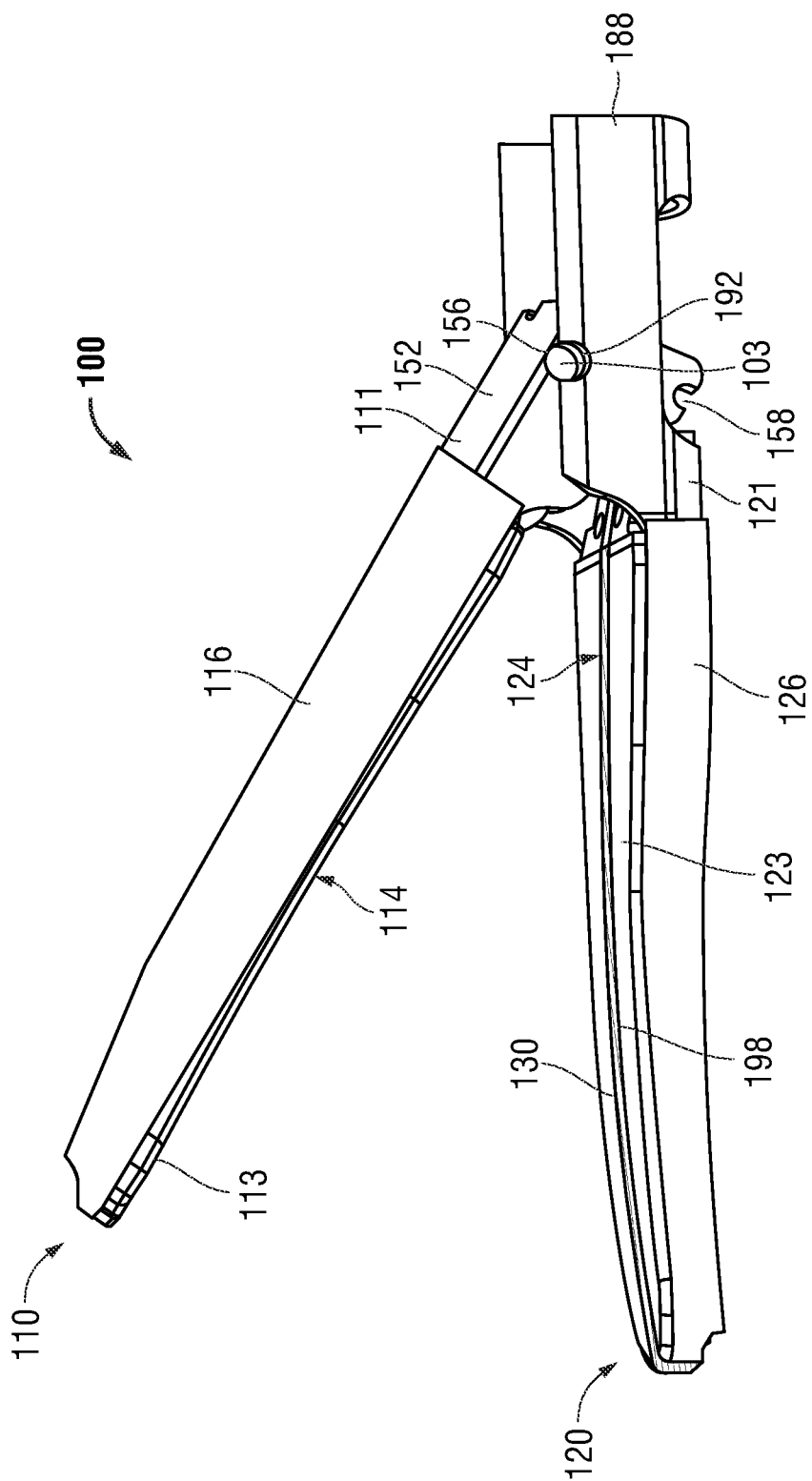
FIG. 4 is a perspective view of an end effector assembly of the forceps of FIG. 1 including first and second jaw members.

Forceps 210 includes two elongated shaft members 212a, 212b, each having a proximal end portion 216a, 216b, and a distal end portion 214a, 214b, respectively. Forceps 210 is configured for use with an end effector assembly 100' similar to and including any of the features of end effector assembly 100 (FIGS. 1 and 4). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212a, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, a first activation switch 280 is provided on one of the shaft members, e.g., shaft member 212a, for supplying energy to jaw members 110', 120' to treat tissue upon sufficient approximation of shaft members 212a, 212b, e.g., upon activation of first activation switch 280 via the other shaft member 212b. A second activation switch 290 disposed on either or both of shaft members 212a, 212b is coupled to the thermal cutting element (not shown, similar to thermal cutting element 130 of jaw member 120 (FIG. 4)) of one of the jaw members 110', 120' of end effector assembly 100' and to the electrosurgical generator "G" for enabling the selective activation of the supply of energy to the thermal cutting element for thermally cutting tissue.

Jaw members 110', 120' define a curved configuration wherein each jaw member is similarly curved laterally off of a longitudinal axis of end effector assembly 100'. However, other suitable curved configurations including curvature towards one of the jaw members 110', 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
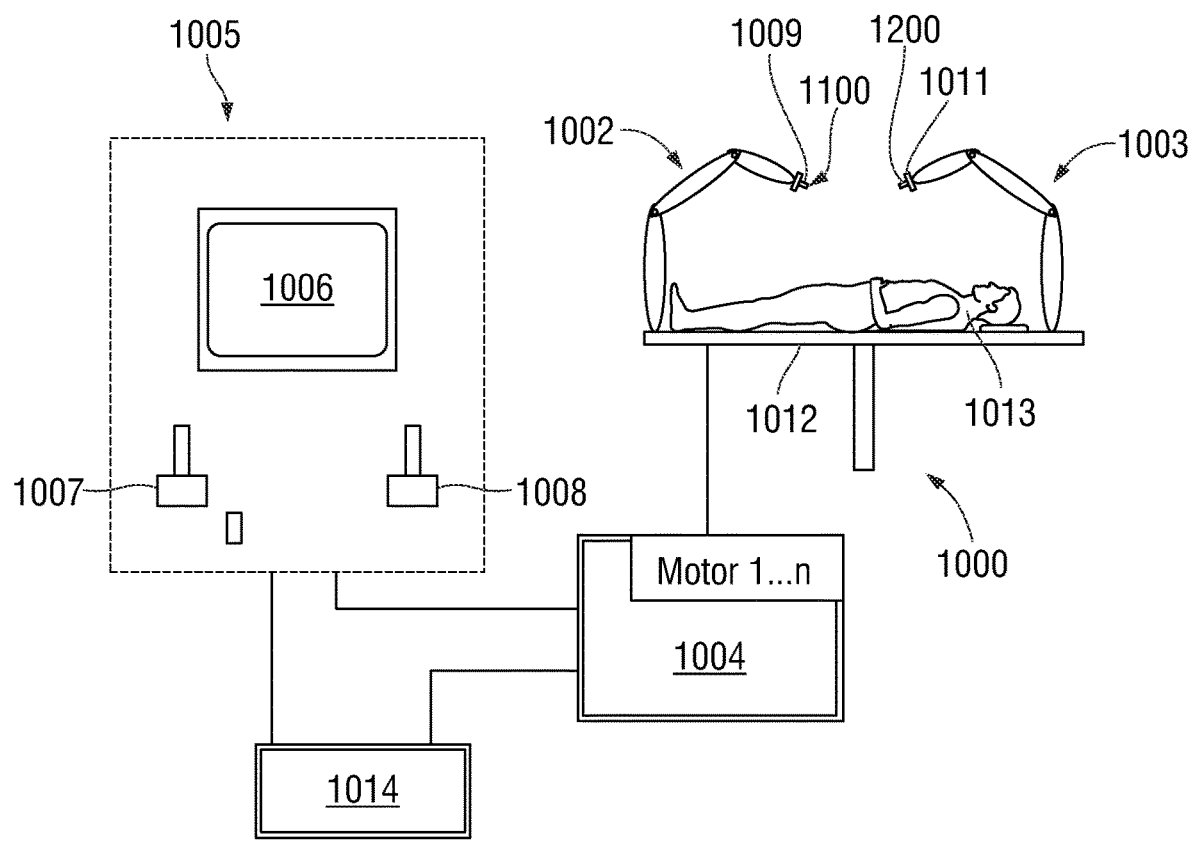
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in an operating mode. Robotic surgical instrument 1000 may be configured for use on a patient 1013 lying on a patient table 1012 to be treated in a minimally invasive manner. Robotic surgical instrument 1000 may further include or be capable of accessing a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to and may include any of the features of end effector assembly 100 (FIGS. 1 and 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Turning to FIGS. 4-9, end effector assembly 100, as noted above, includes first and second jaw members 110, 120. Either or both jaw members 110, 120 may include a structural frame 111, 121, an insulative spacer 112, 122, a tissue treating plate 113, 123 defining the respective tissue treating surface 114, 124 thereof, and, in aspects, an outer insulative jacket 116, 126. Tissue treating plates 113, 123 may be pre-formed and engaged with insulative spacers 112, 122 and/or other portion(s) of jaw members 110, 120 via, for example, overmolding, adhesion, mechanical engagement, etc., or may be deposited onto insulative spacers 112, 122, e.g., via sputtering or other suitable deposition technique.

Referring in particular to FIGS. 4-6B, 8, and 9, jaw member 110, as noted above, includes a structural frame 111, an insulative spacer 112, a tissue treating plate 113 defining a tissue treating surface 114, and, in aspects, an outer insulative jacket 116. Structural frame 111 may be formed from stainless steel or other suitable material configured to provide structural support to jaw member 110. Structural frame 111 includes a proximal flange portion 152 about which jaw member 110 is pivotably coupled to jaw member 120 via pivot 103 and a distal body portion 154 that supports the other components of jaw member 110, e.g., insulative spacer 112, tissue treating plate 113, and outer insulative jacket 116 (where provided). In shaft-based or robotic configurations, proximal flange portion 152 enables operable coupling of jaw member 110 to the drive assembly (not shown) to enable pivoting of jaw member 110 relative to jaw member 120 in response to actuation of the drive assembly. More specifically, proximal flange portion 152 may define an aperture 156 for receipt of pivot 103 and at least one catch 158 for receipt of a drive pin of the drive assembly (not shown) such that translation of the drive pin, e.g., in response to actuation of movable handle 40 (FIG. 1) or a robotic drive, pivots jaw member 110 about pivot 103 and relative to jaw member 120 between the spaced apart position and the approximated position. However, other suitable drive arrangements are also contemplated, e.g., using cam pins and cam slots, a screw-drive mechanism, etc. In hemostat-style devices, proximal flange portion 152 is secured to one of the shaft members, e.g., shaft member 212a of forceps 210 (see FIG. 2). Proximal flange portion 152 may be bifurcated to define a pair of spaced apart proximal flange portion segments or may otherwise be configured.

Distal body portion 154 of structural frame 111 extends distally from proximal flange portion 152 to support the other components of jaw member 110. Distal body portion 154 may define an arcuate transverse, cross-sectional configuration including a concave inner face 162, a convex outer face 164, and a pair of spaced apart longitudinally extending sides 166; however, other configurations, e.g., a squared-off U-shaped configuration, a V-shaped configuration, etc., are also contemplated. Distal body portion 154 further defines an aperture 168 extending at least partially therethrough from concave inner face 162 towards and, in some aspects, through convex outer face 164 (see FIGS. 8 and 9). Distal body portion 154 additionally includes a plurality of cut outs 172 defined through and spaced apart along the lengths of each of sides 166.

Insulative spacer 112 of jaw member 110 is formed from an electrically insulative material capable of withstanding high temperatures, e.g., above at least 300° C., although other configurations are also contemplated. Insulative spacer 112 may be formed from ceramic or other suitable material, e.g., PTFE, PEEK, PEI, etc. Insulative spacer 112 includes a body 174, a pair of overhangs 176 extending outwardly from body 174 and along at least a portion of a length thereof, and a distal cap 178 disposed at the distal end of body 174. Insulative spacer 112 further includes a pair of elongated recesses 180 defined on opposite sides of body 174 on either side thereof. Elongated recesses 180 may be undercut underneath overhangs 176 or otherwise configured.

Continuing with reference to FIGS. 4-6B, 8, and 9, body 174 of insulative spacer 112 is configured for at least partial receipt within concave inner face 162 of distal body portion 154 of structural frame 111 and may be at least partially shaped complementary thereto. Body 174 additionally includes an alignment boss 182 protruding therefrom that is configured for at least partial receipt within aperture 168 of distal body portion 154 of structural frame 111 to facilitate alignment of insulative spacer 112 relative to structural frame 111.

Overhangs 176 of insulative spacer 112 are configured to be supported on longitudinally extending sides 166 of distal body portion 154 of structural frame 111 without obstructing (or without fully obstructing) cut outs 172. Body 174 and overhangs 176 of insulative spacer 112 cooperate to define a face 184 that opposes jaw member 120 in the approximated position. Face 184 may be substantially planar or otherwise configured to support or receive tissue treating plate 113 thereon.

Figure 5:
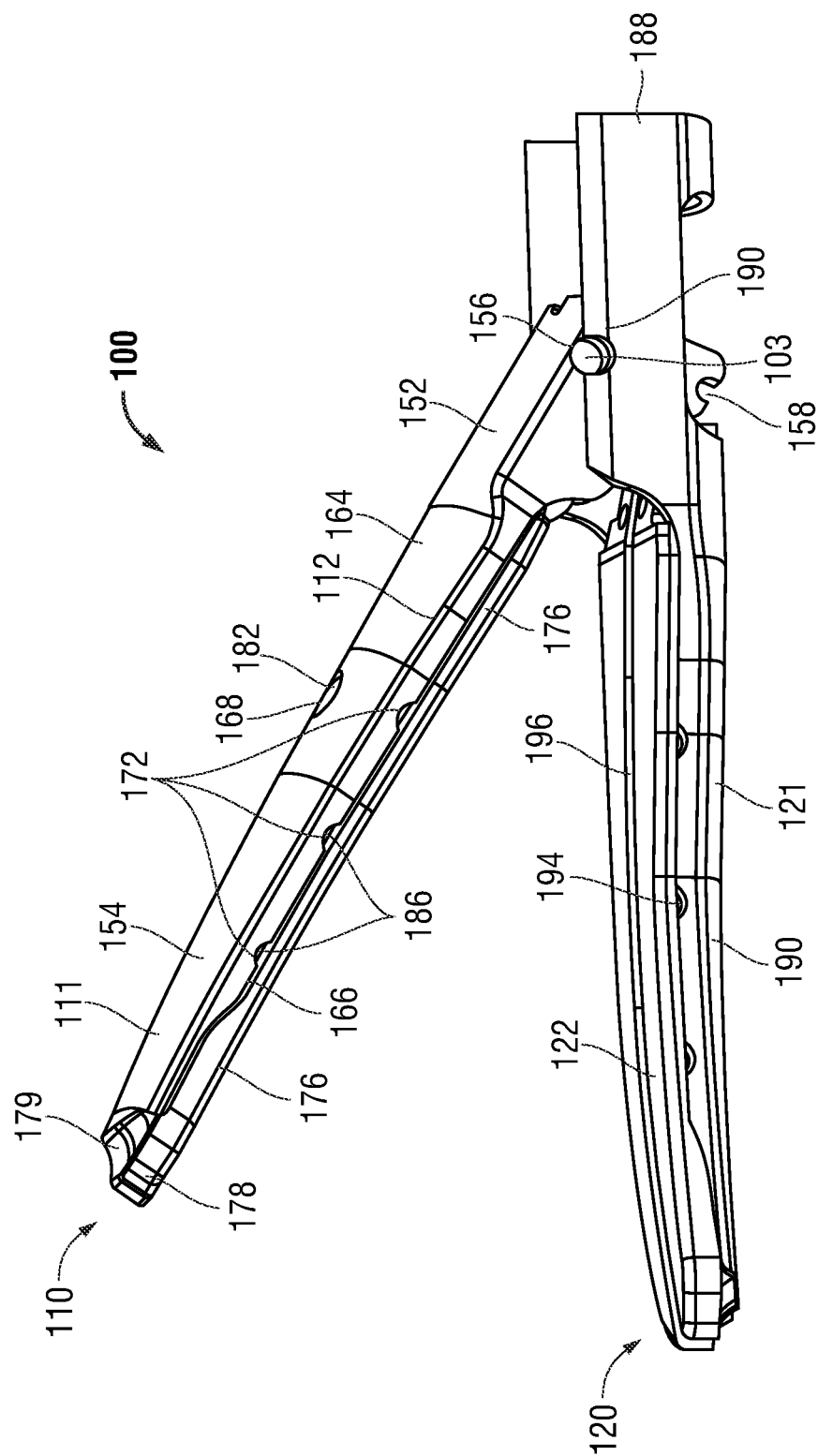
FIG. 5 is a perspective view of the end effector assembly with outer insulative jackets removed from the first and second jaw members and a thermal cutting element removed from the second jaw member.
Figure 6A:
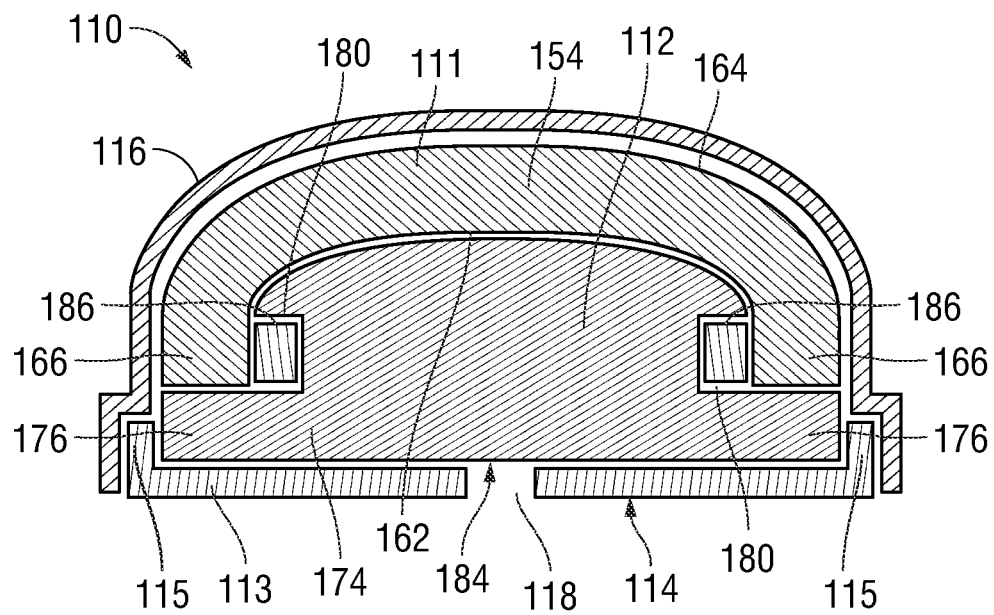
FIG. 6A is a transverse, cross-sectional view of the first jaw member of the end effector assembly as shown in FIG. 4.
Figure 6B:
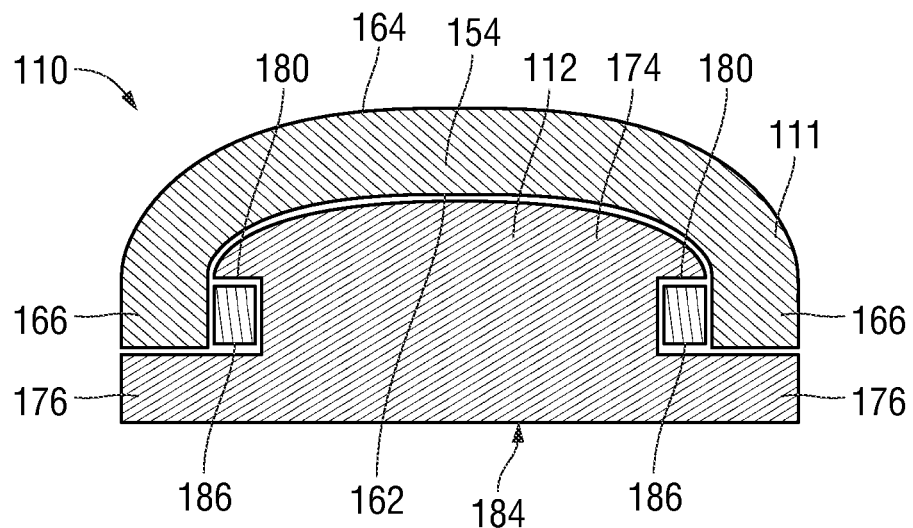
FIG. 6B is a transverse, cross-sectional view of the first jaw member of the end effector assembly as shown in FIG. 5.
Figure 7A:
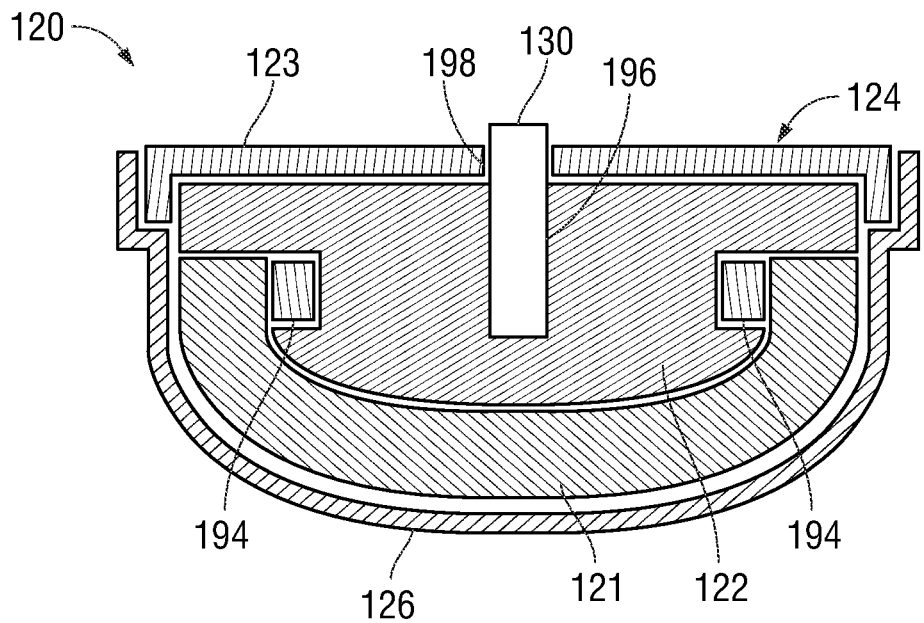
FIG. 7A is a transverse, cross-sectional view of the second jaw member of the end effector assembly as shown in FIG. 4.
Figure 7B:
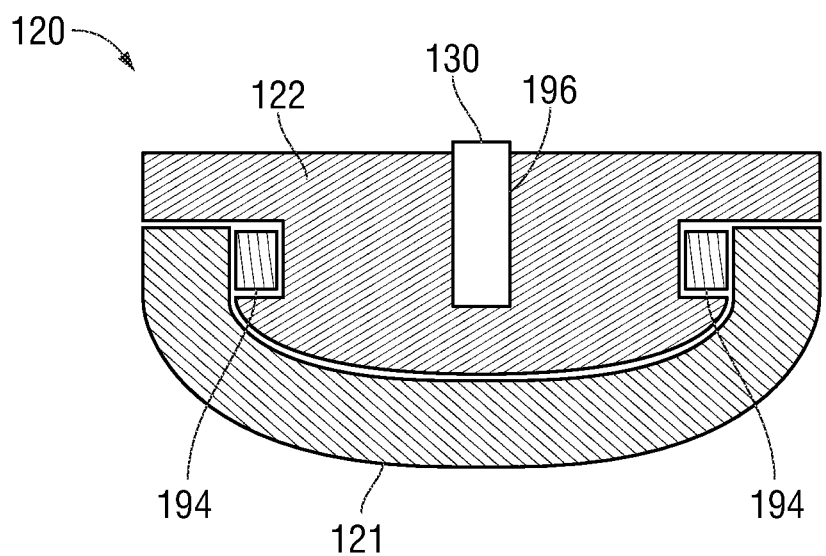
FIG. 7B is a transverse, cross-sectional view of the second jaw member of the end effector assembly as shown in FIG. 5.
Figure 8:
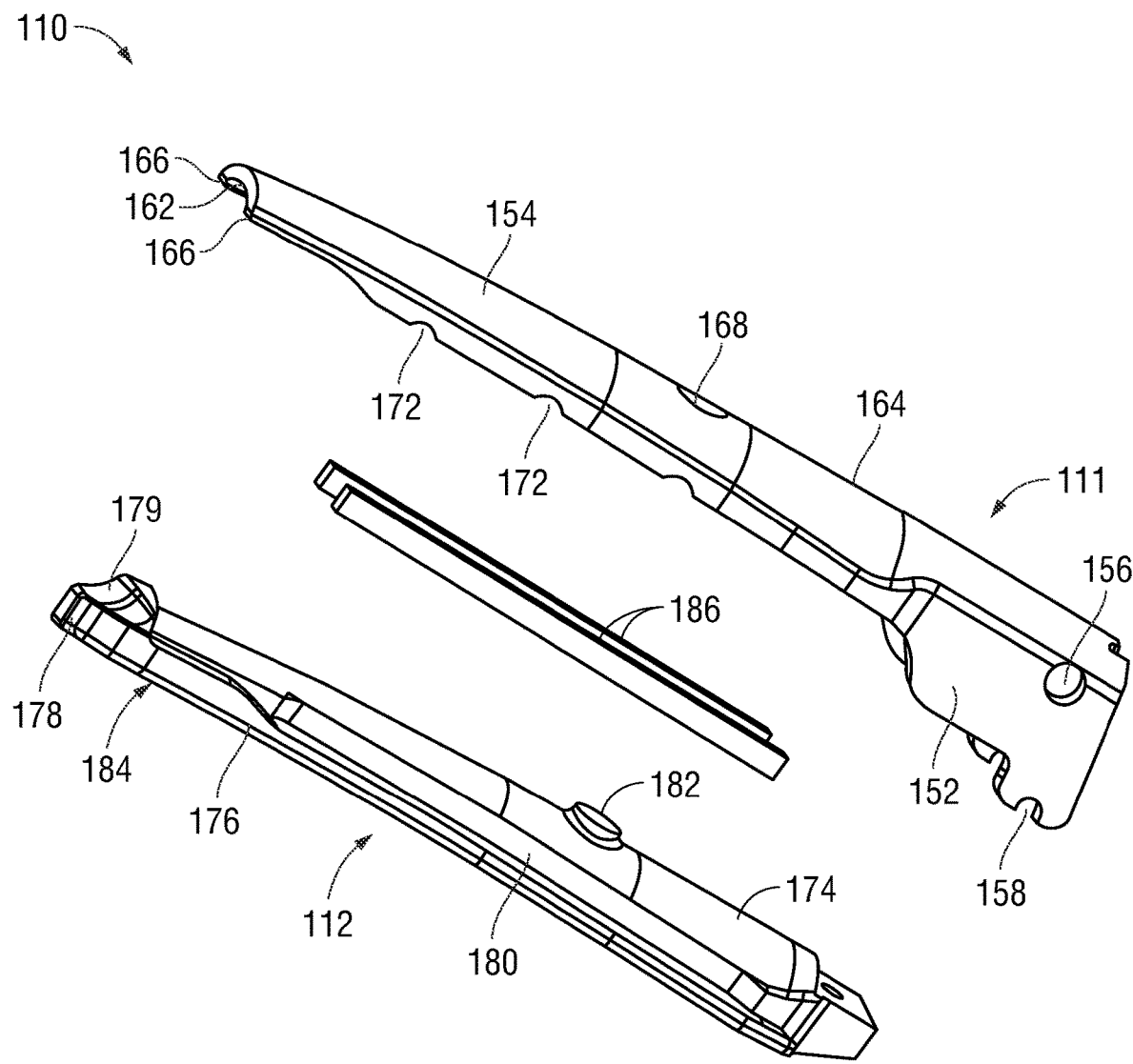
FIG. 8 is an exploded view of the first jaw member of the end effector assembly as shown in FIG. 5.
Figure 9:
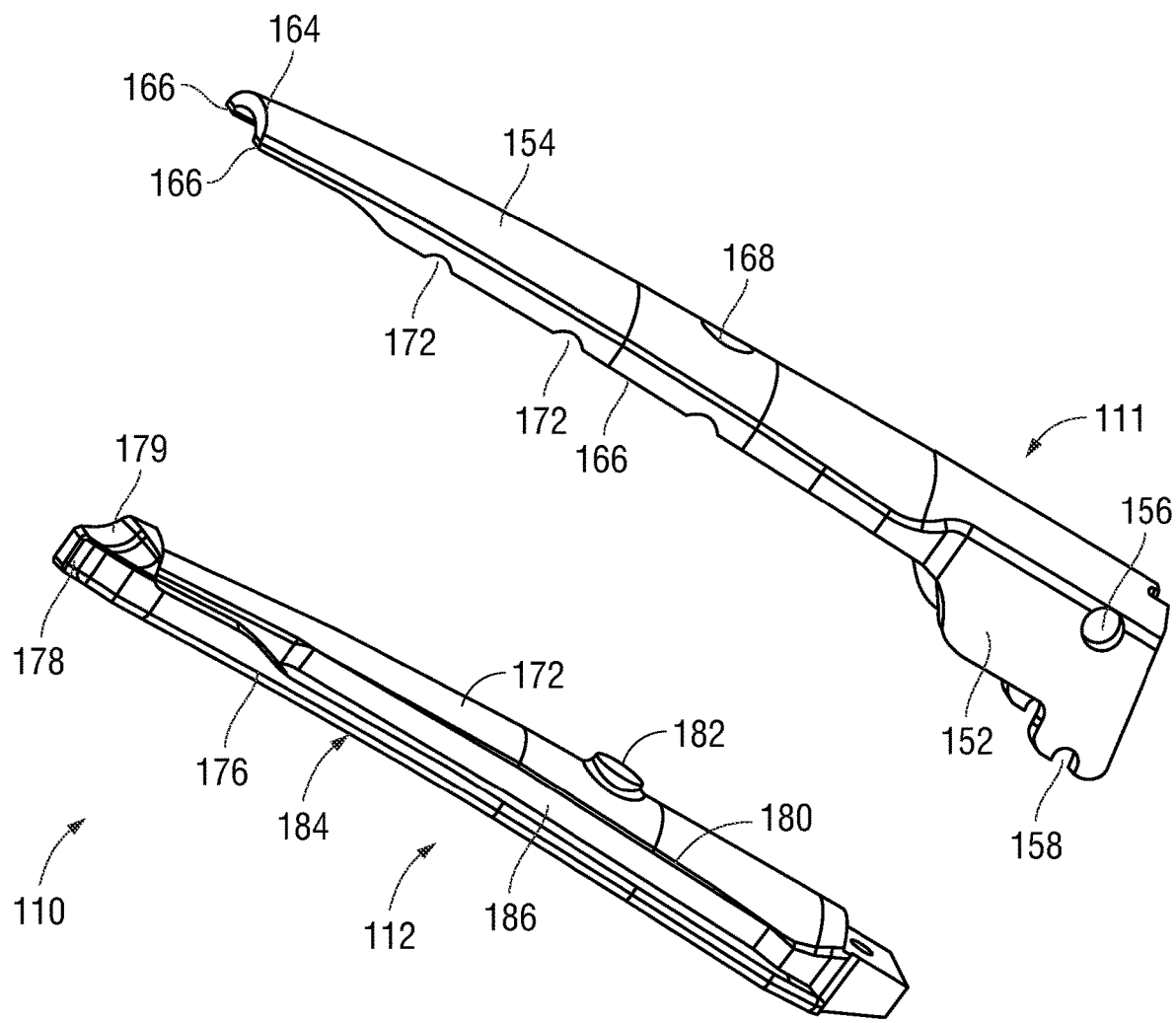
FIG. 9 is a partially exploded view of the first jaw member of the end effector assembly as shown in FIG. 5.

With particular reference to FIGS. 5, 8, and 9, a pair of cleats 186, together with elongated recesses 180 of body 174 of insulative spacer 112 and cut outs 172 of distal body portion 154 of structural frame 111 facilitate attachment of insulative spacer 112 with structural frame 111. Cleats 186 are formed from a metal, e.g., stainless steel, or other suitable material capable of being welded or otherwise attached to structural frame 111. In order to attach insulative spacer 112 to structural frame 111, cleats 186 are inserted into elongated recesses 180 of body 174 of insulative spacer 112, whereby cleats 186 are surrounded on three sides, e.g., the top, bottom, and inner sides, while the outer sides of cleats 186 remain exposed (see FIGS. 8-9). Next, insulative spacer 112, together with cleats 186 therein, is inserted into distal body portion 154 of structural frame 111 such that alignment boss 182 extends at least partially into aperture 168 of distal body portion 154 of structural frame 111, thus ensuring proper alignment of insulative spacer 112 relative to structural frame 111. In aspects, multiple alignment bosses 182 and corresponding apertures 168 may be provided.

With insulative spacer 112, together with cleats 186 therein, inserted into distal body portion 154 of structural frame 111 in proper alignment, portions of cleats 186 are exposed through cut outs 172 of distal body portion 154 of structural frame 111. Cut outs 172 thus provide access to weld or otherwise secure cleats 186 and distal body portion 154 of structural frame 111 to one another. Securing cleats 186 to structural frame 111 thereby secures insulative spacer 112 to structural frame 111 as cleats 186 are received within elongated recesses 180 of body 174 of insulative spacer 112 and surrounded on three sides while structural frame 111 inhibits cleats 186 from backing out of elongated recesses 180.

Distal cap 178 of insulative spacer 112 is configured to at least partially overhang the distal end of distal body portion 154 of structural frame 111 to define the contour of the distal end of jaw member 110 (with or without outer insulative jacket 116 disposed about and confirming to at least a portion of distal cap 178). Distal cap 178 may thus include features to facilitate one or more functions such as, for example, an undercut 179 configured to reduce a thickness of a distal tip of distal cap 178, thereby facilitating blunt dissection utilizing the distal end of jaw member 110. Other features for similar or different purposes are also contemplated.

Referring again to FIGS. 4-6B, 8, and 9, as noted above, tissue treating plate 113 is supported or received on face 184 of insulative spacer 112. In aspects, tissue treating plate 113 includes wings 115 that overlap overhangs 176 of insulative spacer 112 (see FIG. 6A), although other configurations are also contemplated. As noted above, tissue treating plate 113 may be pre-formed and engaged with insulative spacer 112 or may be deposited onto insulative spacers 112, 122, e.g., via sputtering or other suitable deposition technique. In aspects where tissue treating plate 113 is pre-formed and engaged with insulative spacer 112, tissue treating plate 113 may be secured to jaw member 110 and, thus, insulative spacer 112, via overmolding of outer insulative jacket 116 about distal body portion 154 of structural frame 111 and wings 115 of tissue treating plate 113. Tissue treating plate 113 may include a longitudinally extending slot 118 (see FIG. 6A) defined therethrough along at least a portion of the length thereof. Slot 118 may be transversely centered on tissue treating surface 114 or may be offset relative thereto and may be linear, curved, include angled sections, etc. similarly or differently from the configuration, e.g., curvature, of jaw member 110. Slot 118 exposes a portion of insulative spacer 112 and, more specifically, face 184 thereof, which may be recessed relative to tissue treating surface 114, substantially co-planar with tissue treating surface 114, or protruding beyond tissue treating surface 114 towards jaw member 120. In other aspects, slot 118 is omitted and, thus tissue treating plate 113 extends continuously across face 184 of insulative spacer 112 without exposing any portion thereof.

Regardless of the particular configuration of tissue treating plate 113, insulative spacer 112 electrically isolates tissue treating plate 113 from structural frame 111. Tissue treating plate 113 is electrically connected, e.g., via one or more electrical leads (not shown), to first activation switch 80 (FIG. 1) and electrosurgical generator "G" (FIG. 1) to enable selective energization of tissue treating plate 113, e.g., as one pole of a bipolar Radio Frequency (RF) electrosurgical circuit. However, other suitable energy modalities, e.g., thermal, ultrasonic, light, microwave, infrared, etc., are also contemplated.

With reference to FIGS. 4, 5, 7A, and 7B, jaw member 120 includes a structural frame 121, an insulative spacer 122, a tissue treating plate 123 defining tissue treating surface 124, and, in aspects, an outer insulative jacket 126. Jaw member 120 further include thermal cutting element 130.

Structural frame 121 of jaw member 120 defines a proximal flange portion 188 and a distal body portion 190 extending distally from proximal flange portion 188. Proximal flange portion 188 may be bifurcated to define a pair of spaced apart proximal flange portion segments or may define any other suitable configuration. Proximal flange portion 188 of jaw member 120 and proximal flange portion 152 of jaw member 110 may define a nestled configuration, e.g., wherein one of the proximal flange portions 152, 188 is received within the other, an overlapping configuration, e.g., wherein proximal flange portions 152, 188 at least partially overlap one another, or an offset configuration, e.g., wherein proximal flange portions 152, 188 are positioned in side-by-side relation. Regardless of the particular arrangement of proximal flange portions 152, 188, proximal flange portion 188 further defines a cut out 192 configured for receipt of pivot 103, e.g., welded or otherwise secured therein, to pivotably couple jaw members 110, 120 with one another. Proximal flange portion 188 may be secured to shaft 12 (FIG. 1) in shaft-based configurations (or a corresponding shaft portion in robotic configurations); alternatively, a bilateral configuration may be provided whereby both jaw member 110 and jaw member 120 are pivotable relative to shaft 12 (FIG. 1). In hemostat-style configurations, proximal flange portion 188 may be secured to elongated shaft 212b (FIG. 2).

Insulative spacer 122 of jaw member 120 may be configured similarly as and may include any of the features of insulative spacer 112 of jaw member 110 and, thus, only differences therebetween are described below. Further, insulative spacer 122 may be configured to engage structural frame 121 via a pair of cleats 194, similarly as detailed above with respect to insulative spacer 112 of jaw member 110. Insulative spacer 122 differs from insulative spacer 112 at least in that insulative spacer 122 defines a channel 196 configured to receive thermal cutting element 130.

Tissue treating plate 123 defines tissue treating surface 124 and is supported on insulative spacer 122 similarly as tissue treating plate 113 is supported on insulative spacer 112. Tissue treating plate 123 may be formed similarly to and/or include any of the features of tissue treating plate 113 and may be secured to jaw member 120 similarly as tissue treating plate 113 is secured to jaw member 110, e.g., via overmolding of outer insulative jacket 126. Tissue treating plate 123, in particular, defines a longitudinally extending slot 198 (see FIG. 7A) therethrough along at least a portion of the length thereof. Slot 198 may be transversely centered on tissue treating surface 124 or may be offset relative thereto and may be linear, curved, include angled sections, etc. similarly or differently from the configuration, e.g., curvature, of jaw member 120. Slot 198 is aligned with channel 196 and may align with slot 118 of tissue treating plate 113 of jaw member 110 in the approximated position of jaw members 110, 120. Slot 198 exposes a portion of thermal cutting element 130, which may be recessed relative to tissue treating surface 124, substantially co-planar with tissue treating surface 124, or protrude beyond tissue treating surface 124 towards jaw member 110. In aspects where thermal cutting element 130 protrudes, thermal cutting element 130 may contact face 184 of insulative spacer 112 of jaw member 110 (or tissue treating plate 113 of jaw member 110 in aspects where slot 118 is omitted) to set a minimum gap distance, e.g., of from about 0.001 inches to about 0.006 inches, between tissue treating surfaces 114, 124 in the approximated position of jaw members 110, 120.

Insulative spacer 122 electrically isolates tissue treating plate 123 from structural frame 121 and, in aspects, electrically isolates tissue treating plate 123 and thermal cutting element 130 from one another and/or structural frame 121. Tissue treating plate 123 is electrically connected, e.g., via one or more electrical leads (not shown), to first activation switch 80 (FIG. 1) and electrosurgical generator "G" (FIG. 1) to enable selective energization of tissue treating plate 123, e.g., as the other pole of the bipolar (RF) electrosurgical circuit including tissue treating plate 113. In this manner, in the approximated position of jaw members 110, 120 grasping tissue therebetween, bipolar RF electrosurgical energy may be conducted between tissue treating plates 113, 123 and through the grasped tissue to treat, e.g., seal, the grasped tissue. However, other suitable energy modalities, e.g., thermal, ultrasonic, light, microwave, infrared, etc., are also contemplated, as are other suitable tissue treatments, e.g., coagulation.

Thermal cutting element 130 may be secured within and directly to insulative spacer 122 in any suitable manner, e.g., adhesive, friction fitting, mechanical engagement, etc., or may be indirectly secured within insulative spacer 122 via attachment to one or more other components of jaw member 120. Thermal cutting element 130 may protrude distally beyond the distal tip of insulative spacer 122 of jaw member 120, may be substantially flush therewith, or may be recessed relative thereto. In aspects where end effector assembly 100, or a portion thereof, is curved, thermal cutting element 130 may similarly be curved. Thermal cutting element 130 is electrically connected, e.g., via one or more electrical leads (not shown), to second activation switch 90 (FIG. 1) and electrosurgical generator "G" (FIG. 1) to enable selective activation of the supply of energy to thermal cutting element 130 for heating thermal cutting element 130 to thermally cut tissue. Thermal cutting element 130, more specifically, may be configured to cut previously (or concurrently) sealed tissue grasped between jaw members 110, 120, to cut tissue extending across jaw member 120, and/or to cut tissue adjacent the distal end of jaw member 120.

Thermal cutting element 130 may be any suitable thermal cutting element such as, for example, a resistive cutting element, a ferromagnetic cutting element, a monopolar cutting element, a bipolar cutting element, etc. With respect to resistive cutting elements, thermal cutting element 130 may include a substrate, e.g., aluminum, ceramic, stainless steel, etc., an insulative coating disposed on the substrate, e.g., a Plasma Electrolytic Oxidation (POE)-formed coating, a sprayed coating, a deposited coating, or other suitable coating, and a heating circuit trace disposed on the coating such that when an AC voltage is applied to the heating circuit trace, the thermal cutting element 130 is heated for thermally cutting tissue in contact therewith or adjacent thereto.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

What is claimed is:

1. A jaw member of an electrosurgical instrument, comprising:
   an insulative spacer including a face and defining first and second elongated recesses on either side of the face, each of the first and second elongated recesses defined in part by a first surface oriented towards the face of the insulative spacer;
   first and second cleats disposed at least partially within the first and second elongated recesses between the first surfaces of the first and second elongated recesses, respectively, and the face of the insulative spacer;
   a structural frame receiving at least a portion of the insulative spacer therein with first and second elongated sides of the structural frame engaged with the first and second cleats, respectively, whereby the engagement of the structural frame with the first and second cleats and interference between the first surfaces of the first and second elongated recesses and the first and second cleats, respectively, secures the insulative spacer relative to the structural frame with the face exposed; and
   a tissue treating plate disposed on the face of the insulative spacer, the tissue treating plate adapted to connect to a source of energy to treat tissue therewith.

2. The jaw member according to claim 1, wherein the first and second elongated sides are engaged with the first and second cleats, respectively, through cut outs defined within the first and second elongated sides.

3. The jaw member according to claim 2, wherein the first and second elongated sides are welded to the first and second cleats, respectively, through the cut outs.

4. The jaw member according to claim 1, wherein the insulative spacer includes a body and first and second overhangs extending from the body, the body and the overhangs cooperating to define the face.

5. The jaw member according to claim 4, wherein the first and second elongated recesses are undercut below the first and second overhangs, respectively.

6. The jaw member according to claim 1, wherein the structural frame includes a distal body portion configured to receive the at least a portion of the insulative spacer, the distal body portion defining an arcuate configuration including an inner concave face, an outer convex face, and the first and second elongated sides.

7. The jaw member according to claim 1, wherein the structural frame defines an aperture at least partially therethrough and wherein the insulative spacer includes an alignment boss protruding therefrom, the alignment boss received at least partially within the aperture to align the insulative spacer relative to the structural frame.

8. The jaw member according to claim 1, wherein the insulative spacer includes a distal cap that overhangs a distal end of the structural frame to define a distal tip of the jaw member.

9. The jaw member according to claim 1, wherein the tissue treating plate defines a longitudinally extending slot therethrough that exposes a portion of the face of the insulative spacer.

10. The jaw member according to claim 1, further comprising an outer insulative jacket disposed about at least a portion of an outer face of the structural frame, wherein the first and second cleats are formed from a first material and wherein the outer insulative jacket is formed from a second, different material.

11. The jaw member according to claim 1, further comprising an outer insulative jacket disposed about at least a portion of an outer face of the structural frame, wherein the outer insulative jacket and the first and second cleats are separated by the structural frame and the insulative spacer.

12. An electrosurgical instrument, comprising:
   first and second jaw members pivotably coupled to one another such that at least one of the first or second jaw members is movable relative to the other from a spaced-apart position to an approximated position to grasp tissue therebetween, one of the first or second jaw members including:
      an insulative spacer including a face and defining first and second elongated recesses on either side of the face, each of the first and second elongated recesses defined in part by a first surface oriented towards the face of the insulative spacer;
      first and second cleats disposed at least partially within the first and second elongated recesses between the first surfaces of the first and second elongated recesses, respectively, and the face of the insulative spacer;
      a structural frame receiving at least a portion of the insulative spacer therein with first and second elongated sides of the structural frame engaged with the first and second cleats, respectively, whereby the engagement of the structural frame with the first and second cleats and interference between the first surfaces of the first and second elongated recesses and the first and second cleats, respectively, secures the insulative spacer relative to the structural frame with the face exposed; and
      a first tissue treating plate disposed on the face of the insulative spacer,
   wherein the other of the first or second jaw members includes a second tissue treating plate configured to oppose the first tissue treating plate in the approximated position of the first and second jaw members, the first and second tissue treating plates adapted to connect to a source of energy to treat tissue grasped therebetween.

13. The electrosurgical instrument according to claim 12, wherein the one of the first or second jaw members includes an energizable thermal cutting element supported partially within the insulative spacer and extending towards the other of the first or second jaw members.

14. The electrosurgical instrument according to claim 12, wherein the first and second elongated sides are engaged with the first and second cleats, respectively, through cut outs defined within the first and second elongated sides.

15. The electrosurgical instrument according to 14, wherein the first and second elongated sides are welded to the first and second cleats, respectively, through the cut outs.

16. The electrosurgical instrument according to claim 12, wherein the structural frame defines an aperture at least partially therethrough and wherein the insulative spacer includes an alignment boss protruding therefrom, the alignment boss received at least partially within the aperture to align the insulative spacer relative to the structural frame.

17. The electrosurgical instrument according to claim 12, wherein the insulative spacer includes a distal cap that overhangs a distal end of the structural frame to define a distal tip of the one of the first or second jaw members.

18. The electrosurgical instrument according to claim 12, further comprising an outer insulative jacket disposed about at least a portion of an outer face of the structural frame, wherein the first and second cleats are formed from a first material and wherein the outer insulative jacket is formed from a second, different material.

19. The electrosurgical instrument according to claim 12, further comprising an outer insulative jacket disposed about at least a portion of an outer face of the structural frame, wherein the outer insulative jacket and the first and second cleats are separated by the structural frame and the insulative spacer.

* * * * *